US006863864B1

(12) United States Patent
Ingemanson (10) Patent No.: US 6,863,864 B1
(45) Date of Patent: Mar. 8, 2005

(54) METHOD AND APPARATUS FOR INFRARED STERILIZATION

(75) Inventor: Mats O. Ingemanson, New York, NY (US)

(73) Assignee: US Sterlizer Corp., Seaford, DE (US)

( * ) Notice: Subject to any disclaimer, the term of this patent is extended or adjusted under 35 U.S.C. 154(b) by 0 days.

(21) Appl. No.: 09/473,555

(22) Filed: Dec. 29, 1999

Related U.S. Application Data (60) Provisional application No. 60/125,249, filed on Mar. 19, 1999, and provisional application No. 60/114,247, filed on Dec. 30, 1998.

(51) Int. Cl.[7] .................................................. A61L 2/08

(52) U.S. Cl. .................... 422/22; 422/307; 250/455.11; 219/411; 219/553

(58) Field of Search ........................ 250/455.11, 493.1; 426/237, 240, 234, 521; 422/22, 307; 219/411, 553

(56) References Cited

U.S. PATENT DOCUMENTS

| 3,972,127 A | * | 8/1976 | Hoshi et al. ..................... 34/4 |
| 4,501,072 A | * | 2/1985 | Jacobi et al. ................. 34/267 |
| 5,195,165 A | * | 3/1993 | Ono et al. ................... 392/407 |
| 5,811,143 A | * | 9/1998 | Ingemanson ............... 426/241 |
| 5,820,821 A | * | 10/1998 | Kawagoe et al. ............ 422/22 |

* cited by examiner

*Primary Examiner*—Elizabeth McKane
(74) *Attorney, Agent, or Firm*—Law Offices of John A. Parrish (57) ABSTRACT

The disclosed invention relates to sterilization by infrared radiation to eliminate pathogenic bacteria such as *Salmonella*, *E. Coli* 0157:H7 and *E. Coli* (EXEC) from articles such as medical, dental and veterinary instruments, as well as from tableware and eating utensils. The invention further relates to sterilization of soil, military and agriculture equipment to eliminate pathogenic bacteria such as hepatitis, AIDS, and anthrax, and prions such as mad cow disease using infrared radiation. Sterilization is performed by exposing the article to infrared radiation generated from heating elements positioned in an enclosed chamber.

15 Claims, 6 Drawing Sheets

METHOD AND APPARATUS FOR INFRARED STERILIZATION

This application claims benefit of provisional application Ser. No. 60/125,249 filed Mar. 19, 1999, provisional application Ser. No. 60/114,247 filed Dec. 30, 1998.

FIELD OF THE INVENTION

The invention relates to sterilization of objects such as medical, dental and veterinary objects, tableware and eating utensils by infrared radiation to eliminate pathogenic bacteria such as *Salmonella, E. Coli* 0157:H7 and *E. Coli* (EXEC). The invention further relates to sterilization of soil, military and agriculture equipment to eliminate pathogenic bacteria such as hepatitis, AIDS, and anthrax, and prions such as mad cow disease.

BACKGROUND OF THE INVENTION

In treatment of patients in developing countries, concerns exist as to the spread of infection through use of non-sterile instruments. In addition to spread of infection, another concern is contagion from non-sterile instruments is Prion related diseases. Prion or prion related diseases such as Alzheimer disease in humans and mad cow disease in bovine species, although there is no conclusive proof, are suspected of transmission through non-sterile medical, dental and veterinary instruments.

Prions exist normally as innocuous cellular proteins. Prions, however, possess an innate capacity to convert into highly stabile conformations that form harmful particles which become causative agents of several deadly brain diseases of the dementia type in humans and animals. Converted prions are believed to interact with one another to destroy nerve cells in the brain, causing impaired muscle control and dementia-type illnesses. Examples of these types of illnesses include Kuru, Creutzfeldt-Jakob Disease, Fatal Familial Insomnia, Gertsmann-Straussler-Scheinker (GSS) disease, Alzheimer's Disease in humans, Bovine Spongiform Encephalopathy ("mad cow") disease in cattle and Creutzfeldt-Jakob Disease.

A new variant of Creutzfeldt-Jakob Disease may have arisen through mad cow disease transmission. Since 1995 about 20 patients have been identified who exhibit Creutzfeldt-Jakob Disease-like symptoms. These symptoms include psychological problems as well as physical symptoms such as involuntary muscle contractions and difficulties in walking. In addition, new fears have arisen that a strain of Creutzfeldt-Jakob Disease attacks humans under the age of 40.

Most medical practitioners in third world countries treat non-sterile medical instruments with alcohol at room temperature or by boiling water at 100° C. This, however, does not necessarily kill all pathogens such those responsible for various strains of hepatitis.

Instruments also have been sterilized with autoclaves. Autoclaves, however, consume excessive energy and require use of purified water. Autoclaves, moreover, are unable to rapidly sterilize medical instruments.

Rapid sterilization of instruments is important so that those instruments can be used in successive out-patient surgeries in medical offices instead of hospitals. Rapid sterilization also is important in dental offices. In the United States, the Food and Drug Administration requires dentists to sterilize dental hand pieces. Autoclaves, however, can not achieve rapid sterilization. Autoclaves, moreover, due to difficulty in sterilizing the inside mechanics and tubing of hand pieces, can not guarantee sterilization. Autoclaves also corrode the hand pieces. These deficiencies not only endanger patients but also require dentists to procure and inventory excessive number of dental hand pieces. Due to deficiencies such as those discussed above, military and Red Cross field hospitals have found it necessary to use expensive disposable instruments.

Medical, dental and veterinarian instruments, after having been sterilized, must be maintained in a sterilized state over a substantial period of time. This has been accomplished by placing the instruments into a sterility bag prior to and during sterilization.

Sterility bags have been developed for use in autoclaves. These bags, however, are very costly for use in field operations and in developing countries.

Previous efforts to sterilize medical instruments to avoid transmission of mad cow disease from infected instruments have focused on use of elevated temperatures. Tests at the Neuropathogenesis Unit, Institute for Animal Health, Edinburgh, Scotland show only slight inactivation (reduction) of mad cow disease symptoms after treatment of instruments with dry heat or steam heat at 100° C. for 30 minutes. Tests at DLO-Institute for Animal Science and Health (ID-DLO), Lelystad, The Netherlands show only between 1.7 and 3.1 log reduction after 20 minutes pressure cooking at 133° C.

Autoclaves, since they typically are employed to treat instruments with steam at 121° C. for 15 minutes, may not be able to reduce scrapie and other prion agents to a level sufficient to prevent transmission through medical, dental and veterinary instruments of diseases such as Kuru, Gertsmann-Straussler-Scheinker Disease, Fatal Familial Insomnia, Creutzfeldt-Jakob Disease, Bovine Spongiform Encephalopathy, and variants thereof.

Bovine Spongiform Encephalopathy BSE and scrapie agents, as shown by Schreuder BE et al, at DLO-Institute for Animal Science and Health (ID-DLO), Lelystad, The Netherlands, 5-2-1998, are more resistant to lower temperatures and shorter time cycles and less resistant to higher temperatures and longer time cycles.

Yet another concern from contagion is infection from bacteria present in soil and water, especially in third world countries. Anaerobic bacteria such as *B. anthracis* which causes anthrax can form dormant spores (endospores) which can remain viable for long periods of time in soil. Anthrax is 99% lethal to unprotected individuals.

Attempts to control contagion in soil have used methyl bromide. In the United States, about 27,000 tons (60 million pounds) of methyl bromide are used annually in agriculture for soil fumigation, commodity and quarantine treatment, as well as structural fumigation. Globally, about 76,000 tons of methyl bromide are used each year.

Methyl bromide, however, is toxic not only to the target organisms but also to non-target organisms. Human exposure to high concentrations of methyl bromide can result in central nervous system and respiratory system failure, as well as specific and severe deleterious effects to the lungs, eyes, and skin.

In addition, methyl bromide is a significant ozone depleting substance. It is estimated that methyl bromide is at least 50 times more effective at destroying ozone than chlorine from CFCs on a per molecule basis. At the Ninth Meeting of the Parties to the Montreal Protocol, it was agreed that industrialized countries shall completely eliminate use of methyl bromide by the year 2005. Non-industrialized countries shall completely eliminate use of methyl bromide by the year 2015.

Various alternatives to methyl bromide for soil treatment have been or under consideration. Alternatives include 1,3-dichloropropene, dazomet, chloropicrin, and meta sodium, as well as selective contact insecticides and herbicides. For treatment of commodities, alternatives include phosphine and carbonyl sulfide, irradiation, controlled atmospheres utilizing nitrogen and carbon dioxide, & heat/cold. These alternatives, moreover, are pest specific.

In view of the above concerns, it is apparent that a need exists for methods and devices for sterilization of instruments such as medical, dental and veterinarian instruments which avoid disadvantages such as those described above. A need also exists for preserving sterility of medical, dental and veterinary instruments. In addition, a need exists for sterilization of soil, military and agriculture equipment to eliminate pathogenic bacteria as those described above, as well as for sterilization commodities which avoid disadvantages such as those described above.

A concern also exists regarding spread of dangerous bacterium such as *Escherichia Coli* 0157:H7. *Escherichia Coli* 0157:H7 is a dangerous bacterium that is easily spread through consumption of undercooked ground beef and under pasteurized milk. This is particularly so with contaminated ground beef, where the grinding process can spread the virulent bacteria to many hamburger patties processed at the same time. Failure to wash hands or kitchen eating utensils after handling the contaminated meat can also spread the bacterium *Escherichia Coli* 0157:H7 has long been recognized as an important cause of hemolytic uremic syndrome (HUS) and Colitis. According to the Center for Disease Control approximately 20,000 people eat food infected by *E. Coli* 0157:H7 each year. Approximately 200 deaths annually are reported.

*Salmonella enteritidis* is also a major concern. *Salmonella enteritidis* is spread through poultry, eggs, and egg products such as mayonnaise. Eating undercooked poultry, using cooking utensils and cutting boards used for the preparation of raw poultry without properly cleaning them, and eating eggs or egg products which have not been properly refrigerated are the primary causes of infection with *Salmonella enteritidis*.

Other bacterial pathogens can cause food-borne illnesses. For example, *listeria monocytogenes* can cause septicemia, meningitis, and stillbirths. Infections and illnesses from *listeria monocytogenes* often result from unsanitary commercial processing of dairy, poultry, and meat products- including pizza toppings, and kill up to one-third of the people infected and

*Campylobacter jejuni* is now the most common bacterial cause of diarrhea in industrialized countries and is caused by contaminated raw foods. *Campylobacter jejuni* is the most prevalent pathogen in poultry, and in more serious cases, can result in arthritis, septicemia, meningitis, inflammation of the heart and other organs, and Guillain-Barr6 syndrome (paralysis).

Parasitic infections from parasites such as the *Trichinella spiralis* can arise in humans who eat meat from an infected host animal. These parasitic infections can cause permanent damage to the eyes, heart, and other organs. Commercial food processing has greatly reduced the incidence of food-borne parasites; however, foods prepared under unsanitary processing conditions or at home-notably, cured or smoked meat may harbor these parasites.

Food borne pathogens die when exposed to heat for a specific amount of time. A ground beef patty cooked to 160° F. is safe. Cooking of the ground beef patty until it reaches an internal temperature of 160° F. throughout kills *E. Coli* 0157:H7, *Salmonella* and *E. Coli.*

With current technology in the form of broilers, charcoal grills and ovens, however, it is not possible to cook a hamburger patty to the juicy, medium rare state and yet be certain that *E. Coli* 0157:H7, *E. Coli* or *Salmonella* have been killed. In order for the internal temperature of the hamburger patty to reach 160° F., it is necessary to cook the hamburger until reaches the well done state. The well done state, however, is much less juicy and flavorful, and looses its juicy taste.

Food born pathogens such as *Salmonella, E. Coli* 0157:H7 and *E. Coli* (EXEC) can be transmitted by unsanitary tableware and eating utensils. Since these pathogens are resistant to chlorine, then the use of tap water may not be sufficient for cleaning tableware and eating utensils.

A need therefore exists for treating foodstuffs such as hamburger meat to sufficient temperature to kill *E. Coli* 0157:H7, *E. Coli*(EXEC), *Salmonella* and other food borne pathogens and yet avoid the aforedescribed disadvantages.

A need also exists for treating tableware and eating utensils to eliminate pathogens such as *E. Coli* 0157:H7, *E. Coli*(EXEC), *Salmonella* and other food borne pathogens and yet avoid the aforedescribed disadvantages.

SUMMARY OF THE INVENTION

The invention advantageously provides a device and method for sterilizing instruments such as medical, dental and veterinarian instruments as well as soil and commodities. The invention advantageously utilizes much less energy than the autoclaves of the prior art and avoids the need for use of purified water during sterilization. The sterilization device of the invention, having the capacity to sterilize a 16 ounce load of instruments, only consumes electrical energy at the rate of about 1346 Watts/Hour over about 4 minutes for a total energy consumption of only 89.73 Watts. This contrasts with autoclaves which use about 2000 Watts/Hour for 60 minutes for a total of 2000 watts for this same volume of instruments.

The sterilization devices of the invention are especially suited for operation by automobile or portable generator for use in the field for military and humanitarian field applications (for example military or Red Cross field hospitals). The invention, moreover, is exceedingly safe because it does not use steam, pressure or chemicals. Special electrical outlets or vent systems for removal of toxic vapors also are not needed.

The invention advantageously achieves rapid sterilization of instruments such as medical, dental and veterinarian instruments and soil without damage to the instruments. In addition, the sterilization apparatus of the invention can be made in sizes small enough for use in tools and vehicles. The sterilization devices of the invention typically measure about 16.5 inches long, about 10.5 inches wide and about 11.5 inches high and weigh about 20 pounds. Typical autoclaves measure about 24 inches long by 24 inch wide and about 20 inches high and weigh about 80 pounds. The invention can also be employed in equipment which utilized on moving endless belts such as that illustrated schematically in FIG. 7 which employ conveyor belts to sterilize soil on the belt.

In another aspect of the invention, agricultural products are treated to eliminate bacteria therein by exposing those products to infrared radiation at an intensity of about 20–50 $kW/m^2$ generated by a Nichrome-Quartz heating element. These products include, for example, each side of the product is exposed to infrared radiation for a time sufficient to kill the bacteria as well as to cook the agricultural product. The infrared radiation generated in accordance with the invention is particularly suited for sterilizing hamburger meat, ground meat, beef, poultry, and pork of pathogens such as *Salmonella, E. Coli* 0157:H7 and *E. Coli* (EXEC) while also cooking these agricultural products to a flavorful state in about 4 to about 10 minutes.

In another aspect of the invention, articles of tableware and eating utensils are treated to eliminate pathogenic bacteria thereon by exposing those articles to infrared radiation at an intensity of about 20–50 $kW/m^2$ for about 4 minutes to about 20 minutes. Each side of the article is exposed to infrared radiation for a time sufficient to kill bacteria such as *Salmonella, E. Coli* 0157:H7, *E. Coli* (EXEC), hepatitis, *bacillus stearothermophilus* and *Bacillus subtilis*.

Having summarized the invention, it will now be described in detail by reference to the following description.

DETAILED DESCRIPTION OF THE INVENTION

Figure 1:
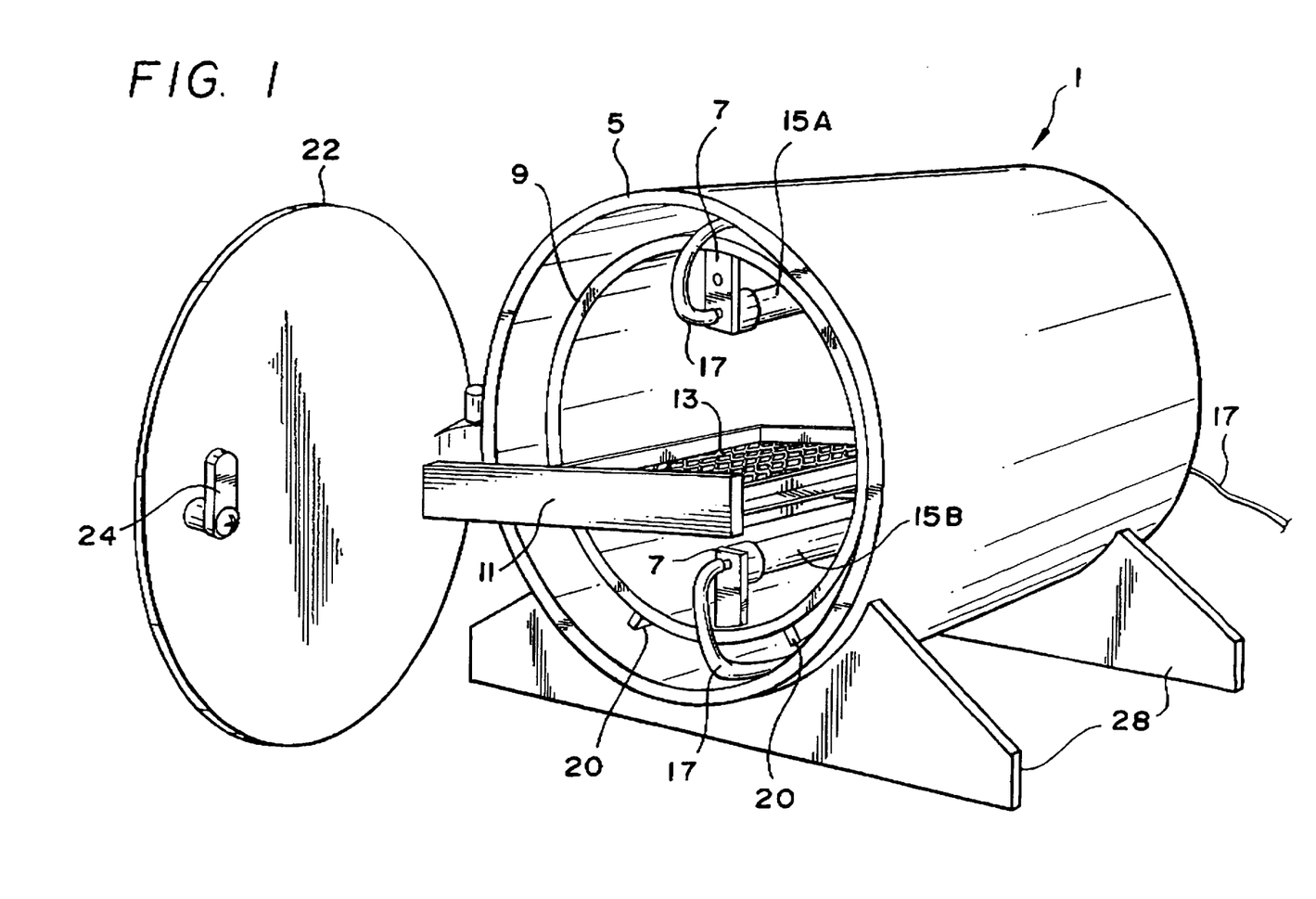
FIG. 1 is a perspective view of the sterilization apparatus of the invention.

In a first aspect of the invention as shown in FIG. 1, sterilization apparatus 1 is provided for sterilization of objects such as medical, dental and veterinarian instruments, as well as tableware and eating utensils by infrared radiation. Apparatus 1 includes inner cylindrical chamber 9 positioned in outer body 5. Chamber 9 is maintained in spaced relationship to outer body 5 by supports 20. Chamber 9 includes elongated support members 42 for receiving and supporting tray 11 therein. Tray 11, preferably having wire mesh 13 therein, can be placed on support members 42 at a desired position in chamber 9. Wire mesh 13 has sufficient thickness to support objects for sterilization thereon. Any ambient atmosphere in chamber 9 optionally may be evacuated so that chamber 9 is in a state of negative pressure.

A single heating element, preferably upper and lower heating elements 15A,15B, respectively, for generating infrared radiation, are supported in chamber 9 by brackets 7. Heating elements 15A,15B receive power through leads 17 connected to a suitable electrical power source (not shown). Sterilization apparatus 1 includes door 22 having lock 24 for closing chamber 9 during operation of apparatus 1. Apparatus 1 may be supported on stands 28.

Heating element 15A, 15B, when electrically energized, generate infrared radiation for delivery to instruments 30 placed in tray 11. Placement of heating elements 15A,15B above and below the instruments provides uniform exposure of the instruments to infrared radiation. Additional heating elements 15A,15B optionally may be placed on the sides of objects 30 to be sterilized. Heating elements 15A,15B preferably are Nichrome-quartz heating elements which include a Nichrome wire housed in a sealed quartz tube. These heating elements typically have a power rating range of about 400 watts to about 800 watts and can generate infrared radiation at an intensity of about 20 $KW/m^2$ to about 50 $KW/m^2$. These elements, when energized to their maximum rated power, operate at about 623° C. to generate infrared radiation at a wavelength of about 3.23 micron at an intensity of about 35.51 $KW/m^2$. Nichrome-quartz heating elements which may be used to generate infrared energy include model Q1M138 from THERMAL Innovations Corporation. Other sources of infrared energy which may be used include halogen lamps, and fossil fuels such as butane, propane, diesel fuel, kerosene and gasoline so that the instruments to be sterilized reach a temperature of about 160° C. which is sufficient for sterilization. Where a fossil fuel is employed, it is injected into a tube or hollow panel such as quartz, Pyrex glass, aluminum, steel or ceramics such as mullite. The tubes or panels can be any of a variety of configurations such as round, oval, elliptical, square, or rectangular. During use, the fuel is injected with air into the tube or panel to create a controlled, prolonged combustion therein to heat the tube or panel. The infrared radiation from the tube or panel functions to sterilize the objects 30.

Heating elements 15A,15B are positioned between chamber 9 and tray 11 as shown in FIG. 1. Chamber 9 is formed from a reflective material such as stainless steel or aluminum, preferably aluminum. Chamber 9 may be flat or it may have curvatures of various radii and configurations such as parabolic and spherical. Preferably, chamber 9 has a spherical radius of curvature of about 3.75 inches. Wire mesh screen 13 can have any mesh size suitable for retaining an 30 to be sterilized thereon. Examples of objects which may be sterilized include but are not limited to medical instruments, dental instruments, veterinarian instruments, soil, and agricultural products such as meats.

Tray 11 having wire mesh 13 with objects 30 thereon can be positioned at a wide range of distances between heating elements 15A,15B to achieve a desired intensity of exposure of instruments 30 to infrared radiation sufficient to sterilize any pathogens on instruments 30. Typically, tray 11 having objects 30 such as medical instruments to be sterilized thereon is located about 2–3 inches, preferably about one inch from heating element 15A and about 3–5 inches, preferably about one inch from lower heating element 15B.

Figures 7, 8:
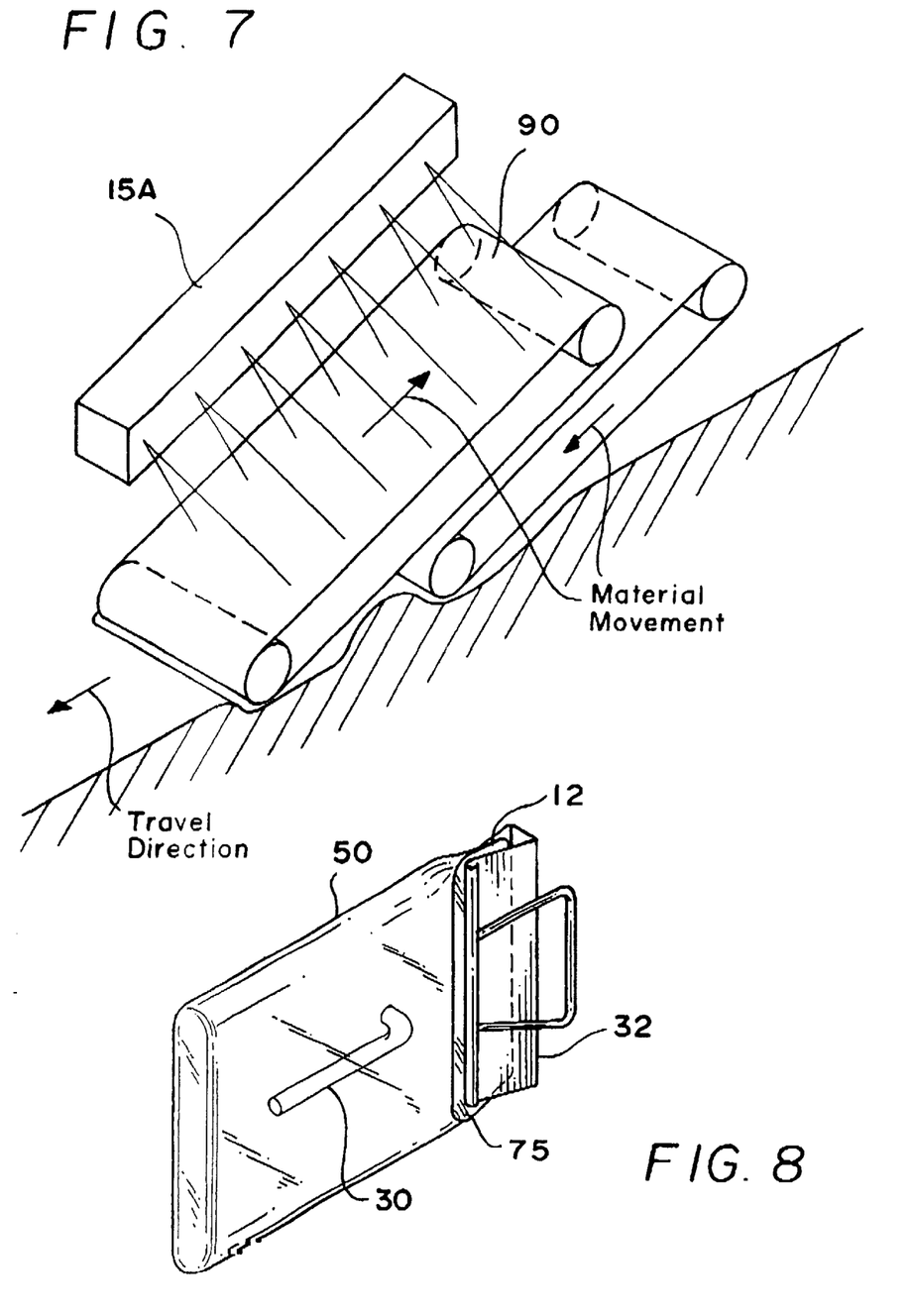
FIG. 7 is a schematic of an alternative embodiment of the sterilsation apparatus of FIG. 1 for use in continuous sterilization of soil.
FIG. 8 shows instruments to be sterilized housed in a sterility bag.

In accordance with another aspect of the sterilization apparatus of the invention, objects 30 to be sterilized are placed in sterility bag 50 as illustrated in FIG. 8 prior to treatment with infrared radiation from elements 15A and 15B.

Sterility bag 50 preferably is re-usable and is formed from Teflon coated fiberglass such as Fluorglas PTFE Coated Glass Fabric 387-3-White Grade from PTFE Coated Fabrics. This material is translucent and enables easy identification of the types of instruments 30 inside sterility bag 50. The material used to make sterility bag 50 can vary in thickness. Useful nominal thicknesses are about 0.08 mm to about 0.43 mm. The sizes of sterility bag 50 also can vary over a wide range. Useful sizes of sterility bag 50 typically measure about 8.5 inches long by about 5.25 inches wide.

Figure 5:
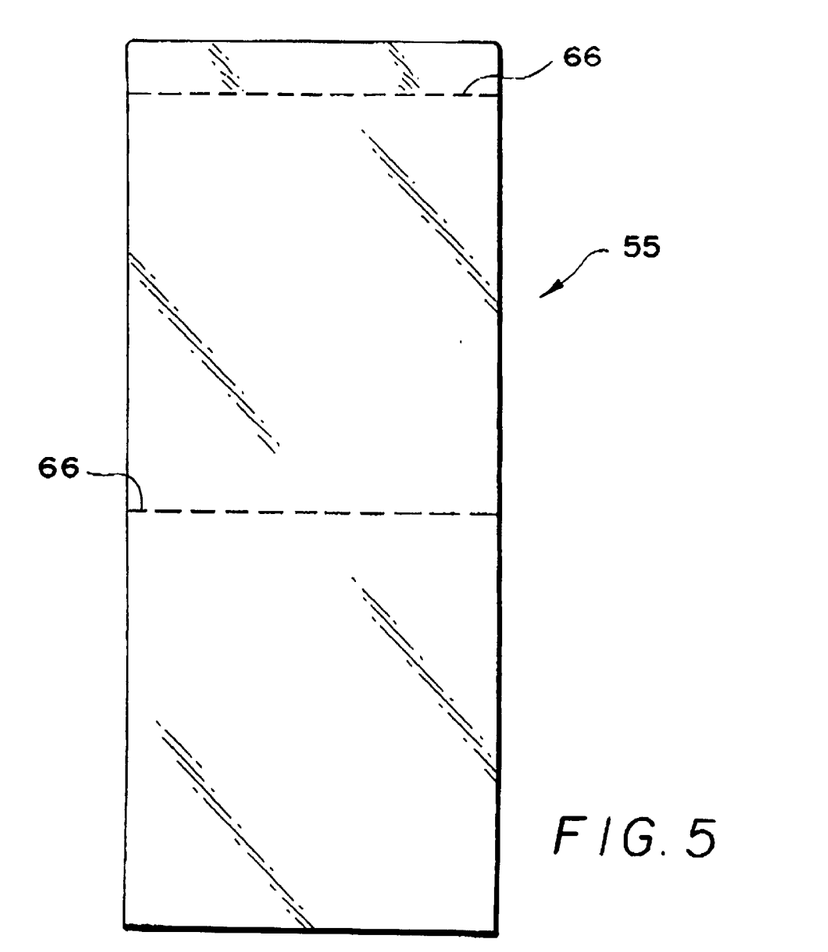
FIG. 5 is a plan view of a sheet of material having fold lines for fabrication into a sterility bag such as that shown in FIG. 5A.

During manufacture of sterility bag 50, sheet material 55 is provided with fold lines 66 as illustrated in FIG. 5. Sterility bag 50 is made by folding sheet material 55 along lines 66, and then heat sealing on three sides and leaving an open end having a flap for sealing the opening. Heat sealing can be done by well-known bag-sealing machines which have heat sealing iron elements heated to about 650° F. to about 700° F. An example of such a bag-sealing machine is the impulse heat sealer from Packworld USA, Nazareth, Pa. 18064.

Figure 5A:
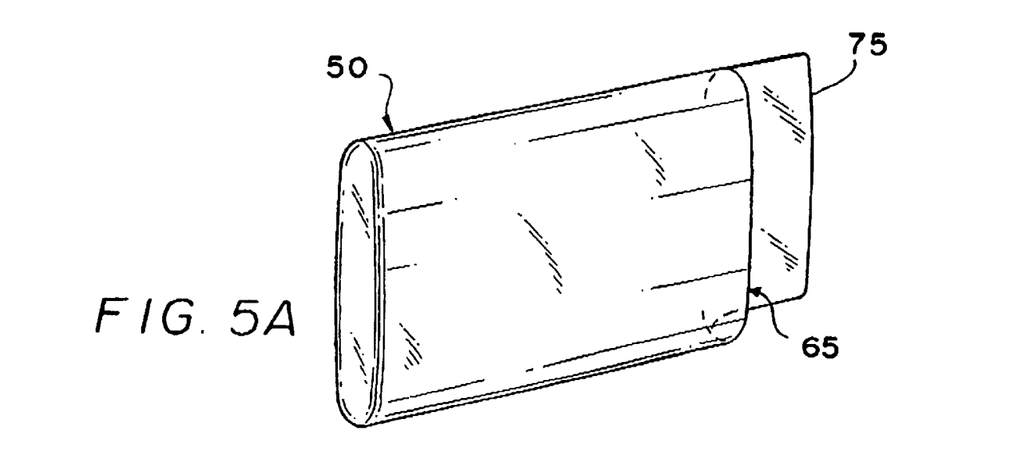
FIG. 5A shows a sterility bag made from the sheet material of FIG. 5.

Sterility bag 50 receives objects 30. After objects 30 are placed in sterility bag 50 through opening 70, flap 75 is sealed over the opening by spring loaded bail type clip 32. Clip 32 can vary in size according to the dimensions of sterility bag 50. The spring loading of clip 32 is sufficient to ensure that clip 32 remains on sterility bag 50 if sterility bag 50 is moved. The jaws of clip 32 also can be made with complementary wavy surfaces to ensure sealing. The jaws of clip 32 also can have pins which extend from one jaw of the clip through the other jaw and corresponding holes in the bag. Sealing of sterility bag 50 by clip 32 ensures that instruments 30 are maintained in a sterile condition inside sterility bag 50 after sterilsation.

Figure 6:
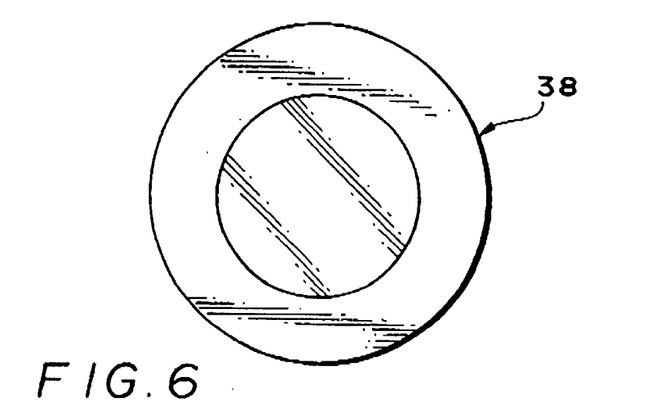
FIG. 6 illustrates a temperature indicator for use with the sterility bag of FIG. 5A.

Sterility bag 50 can be employed with temperature indicator 38 such as that shown in FIG. 6 to measure the temperature of objects 30 in sterility bag 50. Temperature indicator 38 may be chosen from a variety of commercially available products. A product that is particularly useful as temperature indicator 38 is the Single-Point Irreversible Temperature Indicator from Omega Engineering, Inc., PO Box 4047, Stamford, Conn. 06907.

During operation of apparatus 1, objects 30 such as medical, dental and veterinarian instruments are first placed in tray 11 having wire mesh 13 therein. Tray 11 having the objects 30 then is positioned in chamber 9. Door 22 then is secured to close chamber 9. Heating elements 15A,15B then are energized to emit infrared radiation. Objects 30 are exposed to infrared radiation generated by elements 15A, 15B in chamber 9 to cause objects 30 to reach a temperature sufficient for sterilization. Advantageously, sterilization is accomplished with the invention without having to heat the ambient atmosphere of chamber 9 to a temperature sufficient for sterilization. Temperatures for sterilization vary from about 160° C. to about 300° C. depending on the object to be sterilized. In the instance of objects such as metallic medical, dental or veterinarian instruments, the temperature for sterilization is preferably about 210° C.

Infrared radiation from heating elements 15A,15B is applied to objects 30 to cause them to reach at least 160° C., i.e., the temperature sufficient to kill *Bacillus stearothermophilus*. *Bacillus stearothermophilus*, the pathogen that the United States Food and Drug Administration FDA employs to test autoclaves, is the hardest known pathogen for an autoclave to kill. Many other pathogens are killed at much lower temperatures.

Figure 2:
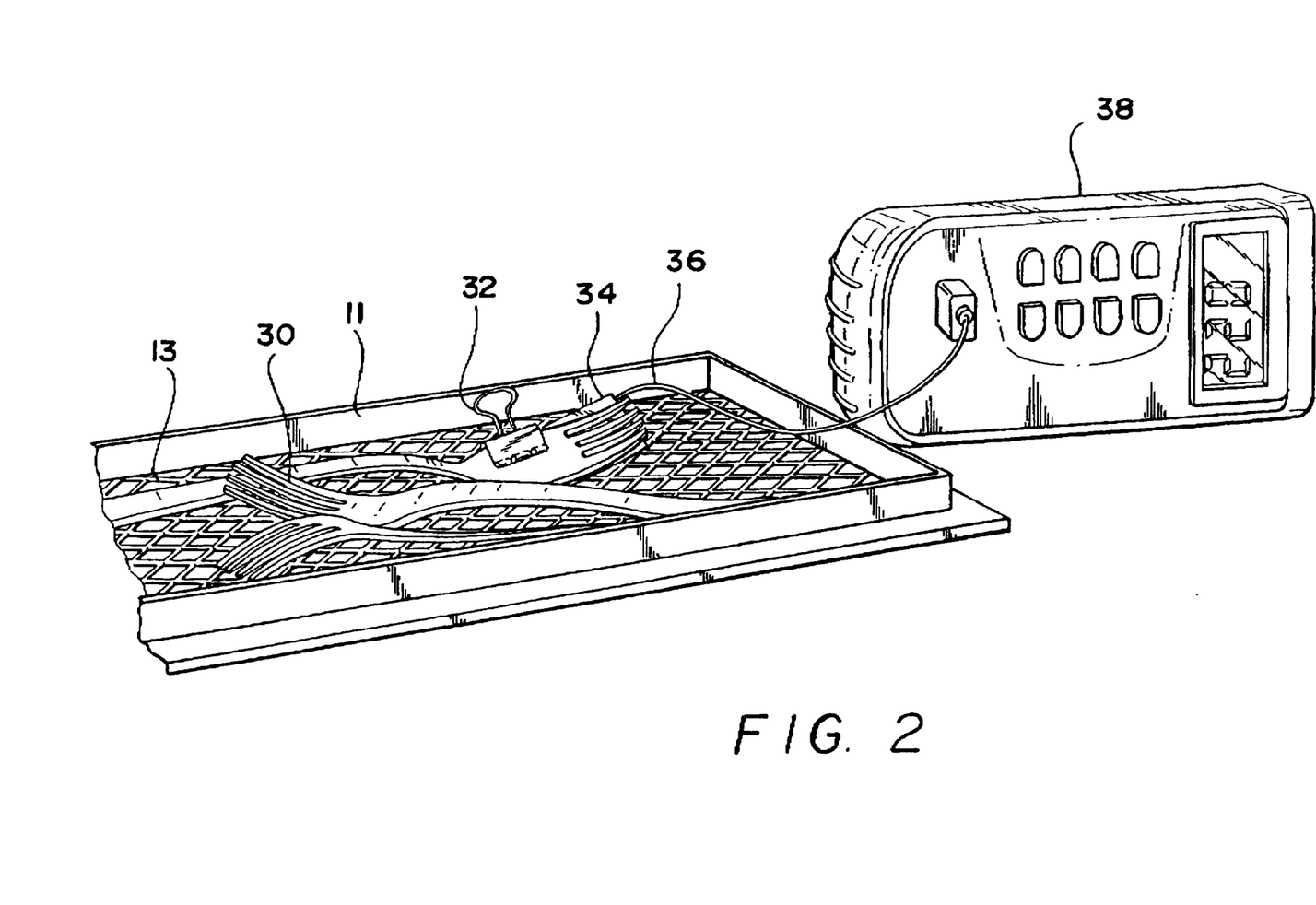
FIG. 2 is a perspective view of the position of a spore strip between metal instruments.
Figure 3:
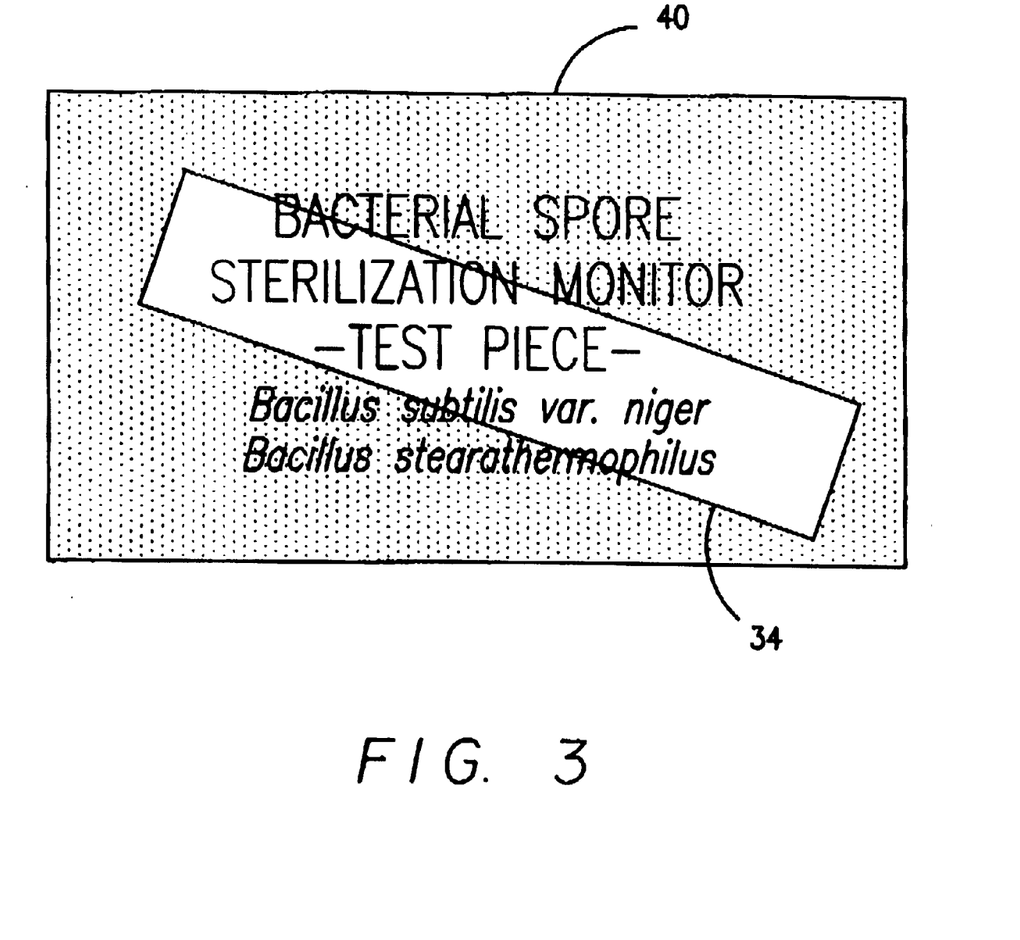
FIG. 3 is frontal view of a spore strip within its glycine bag.
Figure 4:
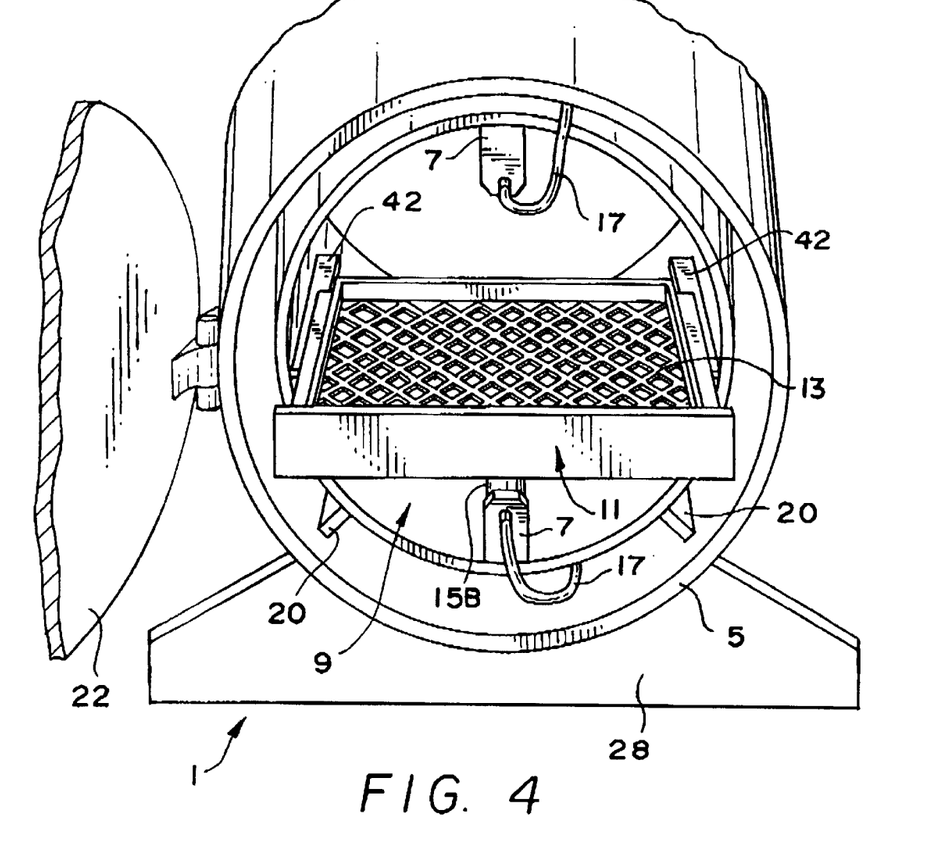
FIG. 4 is a frontal view of the interior of the sterilsation apparatus shown in FIG. 1.

To evaluate the ability of the apparatus and method of invention to achieve rapid sterilization of objects 30, spore strip 34 having *bacillus stearthermophilus* thereon and housed in glycine bag 40 is secured between objects 30 (stainless steel formks) by clip 32 as shown in FIG. 2. Spore strip 34 housed in glycine bag 40 is available as a component of the Spor View Culture Set CS-100 from SPS Medical Corporation, Rochester, N.Y.

Probe 36 of a commercially available instant-read type digital thermometer 38 is inserted between objects 30 to measure the temperature in the region between objects 30 where glycine bag 40 having spore strip 34 is located. The time periods of irradiation, and the temperature of the spore strip 34 are recorded. All tests are initiated from cold starts.

After exposing spore strip 34 to infrared radiation from elements 15A,15B, spore strip 34 is removed from glycine bag 40 and is inserted into a test tube having evaluation liquid as supplied with the above-mentioned SporView Culture Set CS-100. Strip 34 is incubated in the test tube at 56° C. for 48 hours. After incuabtion, if the color of the evaluation liquid changes to yellow, then *Bacillus stearothermophilus* survivors exist on spore strip 34. If the color remains unchanged, then no survivors of *Bacillus stearothermophilus* exist on spore strip 34.

The results are shown in Table 1. All results are for a 16 ounce load of objects 30 (stainless steel instruments). Generally, a heavier load of objects 30 requires more time to reach the desired temperature range of 160° C. to 235° C. For example, the time difference for a 2.5-oz load of stainless steel objects to reach its target temperature and for a 16-oz load stainless steel objects to reach that same target temperature is about 30 seconds.

TABLE 1

| Time (Seconds) | Temp. ° C. | Color of Evaluation Liquid | Result* |
|---|---|---|---|
| 0.0 | 26.0 | Yellow | Survivors |
| 30.0 | 34.0 | Yellow | Survivors |
| 60.0 | 58.0 | Yellow | Survivors |
| 90.0 | 87.0 | Yellow | Survivors |
| 120.0 | 117.0 | Yellow | Survivors |
| 150.0 | 144.0 | Yellow | Survivors |
| 180.0 | 168.0 | Unchanged | No Survivors |
| 210.0 | 190.0 | Unchanged | No Survivors |
| 240.0 | 209.0 | Unchanged | No Survivors |
| 270.0 | 216.0 | Unchanged | No Survivors |
| 300.0 | 214.0 | Unchanged | No Survivors |
| 330.0 | 207.0 | Unchanged | No Survivors |
| 360.0 | 199.0 | Unchanged | No Survivors |
| 390.0 | 191.0 | Unchanged | No Survivors |
| 420.0 | 183.0 | Unchanged | No Survivors |

In order to measure the temperature of instruments 30, probe 36 of instant-read dial type digital thermometer 38 is inserted between instruments 30 to measure the temperature of the region between instruments 30 where spore strip 34 housed in glycine bag 40 is located. Instruments 30 are placed onto wire mesh 13 in tray 11. Heating elements 15A,15B are energized to their maximum power rating of 650 watts for four minutes, and the temperature is read every minute. After four minutes, heating elements 15A, 15B are de-energized and the temperature is read every minute until seven minutes. The temperatures of instruments 30 are shown in Table 2. In Table 2, the weight of the instruments 30 in tray 11 is 16 ounces.

TABLE 2

| Time | Temp. of Instruments |
|---|---|
| 0.0 | 26 (° C.) |
| 60.0 | 58.0 |
| 120.0 | 117.0 |
| 180.0 | 168.0 |
| 240.0 | 209.0 |
| 300.0 | 214.0 |
| 360.0 | 199.0 |
| 420.0* | 183.0 |

*Power turned off.

As a comparison, and in order to determine the role, if any, that the temperature of the air in chamber 9 has in sterilization of objects 30, heating elements 15A, 15B are energized to their full power rating of 650 watts for one minute to reach an operating temperature of 623° C. without tray 11 or instruments 30 present in chamber 9. After the power is turned off, door 22 of apparatus 1 is opened and probe 36 of instant-read dial type digital thermometer 38 is immediately inserted into chamber 9. Door 22 then is closed immediately to measure the air temperature. Apparatus 1 then is cooled to room temperature. This same procedure is repeated for operation times of 2 minutes, 3 minutes and 4 minutes. After 4 minutes the power is turned off. The temperature inside the chamber is read every minute until 7 minutes. The results are shown in Table 3.

TABLE 3

| Time (Sec) | Temp. of Instruments | Temp. of Air In chamber |
| --- | --- | --- |
| 0.0 | 26° C. | 21° C. |
| 60.0 | 58 | 102 |
| 120.0 | 168 | 115 |
| 180.0 | 214 | 121 |
| 240.0 | 209 | 124 |
| 300.0 | 214 | 105 |

*Power turned off

The results in Table 3 show a substantial difference between the temperature of the ambient atmosphere inside chamber 9 and the temperatures of instruments 30 under the same energy and time conditions. After 4 minutes of irradiation as described above, the temperature of the instruments 30 is 209° C. whereas the ambient temperature in chamber 9 is 124° C. After 5 minutes, the temperature of instruments 30 is 214° C. whereas the temperature inside chamber 9 is 105° C.

As can be seen from Table 3, the temperature of the ambient air inside chamber 9 never reached a level high sufficient to sterilize *Bacillus stearothermophilus*. The temperature of instruments 30, however, reached a level more than sufficient to sterilize *Bacillus stearothermophilus*.

Sterilization of Instruments Without Use of a Sterility Bag.

In order to measure the temperature of instruments 30 (dental hand pieces) being sterilized without use of a sterility bag, probe 36 of instant-read dial type digital thermometer 38 is inserted into the hand piece to measure the temperature inside the hand piece where spore strip 34 in glycine bag 40 is located. A 16 oz. load of instruments 30 is placed into tray 11 and placed into chamber 9. Heating elements 15A,15B are energized to 650 watts for 4 minutes, and the temperature of the dental hand pieces is read every minute. After 4 minutes, heating elements 15A,15B are de-energized and the temperature is read every minute until 10 minutes. The temperatures of the dental hand pieces are shown in Table 4. The presence of *Bacillus Stearothermophilus* survivors on spore strip 34 is determined as described above. The results are shown in Table 4.

TABLE 4

| Time (Sec.) | Temp. of Instruments | Result |
| --- | --- | --- |
| 0 | 23° C. | Survivors |
| 30 | 24 | Survivors |
| 60 | 33 | Survivors |
| 90 | 51 | Survivors |
| 120 | 75 | Survivors |
| 150 | 101 | Survivors |

TABLE 4-continued

| Time (Sec.) | Temp. of Instruments | Result |
| --- | --- | --- |
| 180 | 127 | Survivors |
| 210 | 151 | Survivors |
| 240 | 173 | No Survivors |
| 270 | 189 | No Survivors |
| 300 | 193 | No Survivors |
| 330 | 190 | No Survivors |
| 360 | 184 | No Survivors |
| 390 | 176 | No Survivors |
| 420 | 168 | No Survivors |
| 450 | 153 | No Survivors |
| 480 | 125 | No Survivors |
| 510 | 98 | No Survivors |
| 540 | 77 | No Survivors |
| 570 | 60 | No Survivors |
| 600 | 48 | No Survivors |

Sterilization of Objects Within Sterility Bag

In order to measure the temperature of the dental hand pieces in sterility bag 50, probe 36 of an instant-read dial type digital thermometer 38 is inserted inside the dental headpiece to measure the temperature inside the piece where a spore strip 34 housed in glycine bag 40 is located. The hand pieces are placed onto mesh 13 in tray 11 and placed into chamber 9. Heating elements 15A, 15B are energized to their maximum power rating of 650 watts for 4 minutes, and the temperature is read every minute. After 4 minutes, the heating elements 15A,15B are de-energized and the temperature is read every minute until 20 minutes. The temperatures of the hand pieces are shown in Table 5. In Table 5, the weight of the hand pieces inside sterility bag 50 is 10.5 ounces. The presence of *Bacillus Stearothermophilus* survivors on spore strip 34 is determined as described above. The results are shown in Table 5. The data in Tables 4 and 5 show that sterilization times are not extended when using sterilization bag 40.

TABLE 5

| Time (sec) | Temp (° C.) | Result |
| --- | --- | --- |
| 0 | 25 | Survivors |
| 30 | 26 | Survivors |
| 60 | 34 | Survivors |
| 90 | 53 | Survivors |
| 120 | 80 | Survivors |
| 150 | 105 | Survivors |
| 180 | 134 | Survivors |
| 210 | 162 | No Survivors |
| 240 | 190 | No Survivors |
| 270 | 212 | No Survivors |
| 300 | 222 | No Survivors |
| 330 | 224 | No Survivors |
| 360 | 221 | No Survivors |
| 390 | 216 | No Survivors |
| 420 | 211 | No Survivors |
| 450 | 204 | No Survivors |
| 480 | 195 | No Survivors |
| 510 | 185 | No Survivors |
| 540 | 174 | No Survivors |
| 570 | 163 | No Survivors |
| 600 | 153 | No Survivors |
| 630 | 143 | No Survivors |
| 660 | 135 | No Survivors |
| 690 | 127 | No Survivors |
| 720 | 122 | No Survivors |
| 750 | 117 | No Survivors |
| 780 | 113 | No Survivors |
| 810 | 109 | No Survivors |
| 840 | 105 | No Survivors |
| 870 | 101 | No Survivors |

TABLE 5-continued

| Time (sec) | Temp (° C.) | Result |
|---|---|---|
| 900 | 97 | No Survivors |
| 930 | 94 | No Survivors |
| 960 | 91 | No Survivors |
| 990 | 88 | No Survivors |
| 1020 | 85 | No Survivors |
| 1050 | 82 | No Survivors |
| 1080 | 79 | No Survivors |
| 1110 | 76 | No Survivors |
| 1140 | 73 | No Survivors |
| 1170 | 71 | No Survivors |
| 1200 | 69 | No Survivors |

Sterilization of soil infected with *Fusarium*, Trichderma and *Pythium*

In this aspect, the apparatus and method of the invention are used to sterilize soil samples infected with *Fusarium*, Trichderma and *Pythium* which were obtained from the United States Dept. of Agriculture Forest Service, Technology & Development Center, Fort Missoula, Missoula, Mont. The soil samples contained 274.3 cfu/g *Fusarium*, 68.6 cfu/g Trichderma and 13.7 cfu/g *Pythium*. These soil samples are treated with infrared radiation from heating elements 15A, 15B in chamber 9 of apparatus 1. The soil samples are spread onto tray 11 to form a layer of about ⅛ inch to about ¼ inch thick. Tray 11 having the soil sample is placed into chamber 9. The soil sample is 3.25 inches from heating element 15A and 1.25 inches from heating element 15B. Heating elements 15A,15B are energized to emit infrared radiation at an intensity of 28.8 KW/m².

Six soil samples are treated using differing time intervals of exposure to the infrared radiation from elements 15A, 15B as above. The soil samples are returned to the United States Dept. of Agriculture Forest Service, Technology & Development Center, Fort Missoula, Missoula, Mont. where they are evaluated for residual *Fusarium, Trichoderma* and *Pythium*. Evaluation for presence of *Fusarium, Trichoderma* and *Pythium* entails oven drying a 5 gram sample of the irradiated soil at 100° C. for at least 24 hours or until the sample weight stabilizes and all excess moisture is removed. Oven-dry weight is calculated to provide a standard for comparison. For assay of *Fusarium* and *Trichoderma*, 0.05 g of field-moist soil is combined with 10 ml of 0.3% water agar and thoroughly mixed to provide a liquid mixture. One ml of the liquid mixture is placed on each of three plates of selective agar medium and spread uniformly. The plates are incubated for 5 days at about 24° C. under diurnal cycles of cool, fluorescent light. *Fusarium* and *Trichoderma* colonies are identified by their morphology on the selective medium and populations calculated. *Fusarium* isolates are transferred to carnation leaf agar and potato dextrose agar for identification using the taxonomic scheme of Nelson disclosed in *Fusarium* Species: An Illustrated manual for Identification, Pennsylvania State University Press, University park, PA Page 193(1983). For assay of *Pythium* populations, 0.5 g of soil is combined with 10 ml of 0.3% water agar. One ml of solution is placed on each of three plates of another selective medium of V-8 juice agar amended with pimaricin, rifamycin, ampicillin and pentchloronltrobenze as disclosed by James et al. in Soil Assays for *Fusarium* and *Pythium* in fumigated soils, Forest Pest Management, Nursery Disease Notes, No. 16, Page 3(1985). Plates are incubated in darkness at about 24° C. for 3 days. *Pythium* colonies are identified on the basis of their diameter after three days (15–20 mm), their feather margin, and their growth within the Agar medium rather than superficially on the surface of the agar medium. It is assumed that each colony originates from an individual propagule. Populations are expressed as colony-forming units (cfu) per gram of oven dried soil.

The results, as shown in Table 6, show that when the soil samples are subjected to infrared radiation at an intensity of 28.8 kW/m² in the apparatus of the invention completely kill *Fusarium* and Trichderma in the soil samples is achieved after 27 seconds exposure, and that complete kill of *Pythium* is achieved after 20 seconds exposure.

In an alternate embodiment of this aspect of the invention, the soil to be sterilized can be placed on a continuous belt 90 and exposed to infrared radiation as shown schematically in FIG. 7.

TABLE 6

| Time (Sec.) | Residual *Fusarium* | Residual *Trichderma* | Residual *Pythium* | Intensity of Infrared Radiation | Soil Volume |
|---|---|---|---|---|---|
| 20 | 136.2 | 408.6 | 0 | 28.8 | ½ Pint |
| 23 | 205.9 | 0 | 0 | 28.8 | ½ Pint |
| 24 | 68.1 | 68.1 | 0 | 28.8 | ½ Pint |
| 27 | 0 | 0 | 0 | 28.8 | ½ Pint |
| 55 | 0 | 0 | 0 | 28.8 | ½ Pint |
| 66 | 0 | 0 | 0 | 28.8 | ½ Pint |
| Control | 274.3 | 68.6 | 13.7 | No treatment | ¾ Pint |

In another embodiment, and to show the ability of the invention to eradicate anthrax spores from soil, *Bacillus subtilis* is placed inside bacterial sterilization monitor spore strips from SPS Medical Corporation. *Bacillus subtilis* was chosen because the U.S. Army Medical Research Institute of Infectious Diseases at Fort Detrick regards *Bacillus subtilis* as a surrogate for anthrax. The spore strips having *bacillus subtilis* thereon are inserted between two stainless steel metal blades. The metal blades were tightly fitted together prior to sterilization. The spore strips located between the metal blades are exposed to infrared radiation generated by the Nichrome-quartz heating elements at an intensity of 35.51 KW/m² for 4–5 minutes. After irradiation, the spore strips were incubated at 37° C. for 96 hours in a test tube filled with color indicator liquid. The color indicator liquid is included in the Sporview Culture Set available from SPS Medical, Rochester, N.Y. All tests were initiated from cold starts. The presence of *bacillus subtilis* survivors on the irradiated spore strip is determined using the procedure described above as described above in connection with *bacillus stearothermophilus*. The results are shown in Table 7.

The results in Table 7 show that *bacillus subtilis* is eradicated after 3.5 minutes.

TABLE 7

| Time (min:sec) | Temp ° C. | Residual *Bacillus Subtilis* |
|---|---|---|
| 0:00 | 26 | Survivors |
| 0:30 | 34 | Survivors |
| 1:00 | 58 | Survivors |
| 1:30 | 87 | Survivors |
| 2:00 | 117 | Survivors |
| 2:30 | 144 | Survivors |
| 3:00 | 168 | Survivors |
| 3:30 | 190 | No Survivors |
| 4:00 | 209 | No Survivors |
| 4:30 | 216 | No Survivors |
| 5:00 | 214 | No Survivors |
| 5:30 | 207 | No Survivors |

TABLE 7-continued

| Time (min:sec) | Temp ° C. | Residual Bacillus Subtilis |
|---|---|---|
| 6:00 | 199 | No Survivors |
| 6:30 | 191 | No Survivors |
| 7:00 | 183 | No Survivors |

The invention, in addition to rapid sterilization, makes energy transfers for sterilization more effective and treatment cycles shorter without toxicity or radioactivity. The invention is environmentally safe and does not damage the Ozone layer.

The invention enables planting of, for example, tomatoes, strawberries, peppers, nursery trees, carrots, seedbeds, lettuce, tobacco, sweet potatoes, melons, cucumbers, eggplants, cantaloupe, cauliflower, broccoli, onions and other crops in soil immediately after the soil is sterilized by the apparatus and method of the invention. This is in contrast to a waiting period of three weeks when planting in soil that has been sterilized with Methyl Bromide.

The small size and lightweight of the apparatus of the invention in combination with its low energy consumption, makes the invention uniquely suitable for use in field hospitals to sterilize medical, dental and veterinary instruments. The apparatus of the invention can be scaled to large sizes when employed in high volume applications such as sterilization of soil.

The invention, due in part to its ability to achieve rapid sterilization in less than 3.5 minutes can be used to prevent transmissions of mad cow disease via medical, dental and veterinary instruments. Both the temperature range and time cycle of the apparatus may be varied to eliminate contagion believed to contribute toward Alzheimer's Disease, Bovine Spongiform Encephalopathy (BSE—Mad Cow Disease), Kuru, Gertsmann-Straussler-Scheinker Disease, Fatal Familial Insomnia, Creutzfeldt-Jakob Disease (CJD), a new variant of CJD and harmful prions on medical, dental and veterinary instruments (better than 8.0 log).

In another aspect of the invention, agricultural products, preferably hamburger meat, ground meat, beef, poultry, and pork are treated with infrared radiation in apparatus 1 using infrared radiation generated by heating elements 15A, 15B. Preferably, the heating element is a Nichrome wire housed in a quartz tube. The Nichrome heating element also may be housed in a ceramic tube such as mullite.

In an illustrative aspect of the invention, a 4 oz. Hamburger patty is placed on tray 11 having wire mesh 13 therein. Tray 11 is inserted into apparatus 1 so that the patty is located 3.25 inches from top heating element 15A and 1.25 inches from lower heating element 15B. Elements 15A,15B are energized to 650 watts at 123 V each to generate infrared radiation at an intensity of 36.83 KW/m$^2$ onto the hamburger patty for a time sufficient to reach a sterilization temperature of about 158° F. to about 176° F.

The temperature inside the hamburger patty was measured with probe 36 of instant-read dial type digital thermometer 36 inserted into the middle of the hamburger patty. The probe and thermometer also are used to check temperatures throughout the patty. After subjecting the hamburger patty to the infrared radiation as described above for 270 sec., the temperature in every portion of the hamburger patty was 160° F. or above. The results of treatment of the hamburger patties cooked to the medium rare state are shown in Table 8.

TABLE 8

| Time | Temp ° F. |
|---|---|
| 0 sec. | 47 |
| 30 | 65 |
| 60 | 86 |
| 90 | 103 |
| 120 | 118 |
| 150 | 130 |
| 180 | 141 |
| 210 | 148 |
| 240 | 155 |
| 270 | 162 |

What is claimed is:

1. An apparatus for sterilizing by infrared radiation comprising, a chamber 9 adapted for receiving a plurality of heating elements 15A,15B for generating infrared radiation, heating elements 15A,15B comprising Nichrome wire housed in a sealed tube that consists essentially of quartz, heating elements 15A,15B capable of generating infrared radiation at a wavelength of about 3.23 micron and at intensity of about 20 KW/m$^2$ to about 50 KW/m$^2$, the chamber 9 having means to support a tray 11 comprising wire mesh 13 positioned in tray 11 for holding an object to be sterilized, the chamber 9 also having a spherical reflecting surface having a radius of curvature of about 3.75 inches for reflecting infrared radiation from heating elements 15A,15B onto the object to be sterilized.

2. A method for sterilizing an object of pathogens by infrared radiation comprising, exposing an object having a pathogen to be sterilized to infrared radiation within an apparatus 1 having a chamber 9 wherein the infrared radiation is generated by heating elements 15A, 15B located in chamber 9 to cause the object to reach a temperature sufficient to sterilize the object of pathogens without causing ambient atmosphere in chamber 9 to reach at a temperature sufficient to sterilize the object of pathogens, wherein the heating elements 15A,15B comprise Nichrome wire housed in a sealed tube that consists essentially of quartz and generate infrared radiation at a wavelength of about 3.23 micron.

3. The method of claim 2 wherein the temperature is about 160° C.

4. The method of claim 2 wherein the heating elements 15A,15B generate infrared radiation at an intensity of about 20 KW/m$^2$ to about 50 KW/m$^2$.

5. The method of claim 4, wherein the heating elements 15A,15B cause the objects to be sterilized to reach about 160° C.

6. The method of claim 2 wherein the pathogen is any of Salmonella, E. Coli 0157:H7, E. Coli (EXEC), hepatitis, anthrax, and prions.

7. The method of claim 6 wherein the object to be sterilized is any of medical instruments, dental instruments, veterinary instruments, tableware, eating utensils, and soil.

8. A method for sterilizing an object of pathogens by infrared radiation comprising, exposing an object having a pathogen to be sterilized to infrared radiation from heating elements 15A,15B located in chamber 9 housed in an apparatus 1, the infrared radiation having a wavelength of about 3.23 micron and an intensity of about 20 KW/M2 to about 50 KW/m$^2$, the heating elements 15A, 15B comprising Nichrome wire housed in a sealed tube that consists essentially of quartz, wherein the exposing is sufficient to cause the object to reach about 160° C. without causing any ambient atmosphere in chamber 9 to 160° C., and wherein the pathogen is any of *Salmonella, E. Coli* 0157:H7, *E. Coli* (EXEC), hepatitis, anthrax, and prions, and wherein the object to be sterilized is any of medical instruments, dental instruments, veterinary instruments, tableware, eating utensils, and soil.

9. A method for sterilizing an object of pathogens by infrared radiation comprising, exposing an object having a pathogen to be sterilized to infrared radiation within an apparatus 1 having a chamber 9 wherein the infrared radiation is generated by heating elements 15A, 15B located in chamber 9 to cause the object to reach a temperature sufficient to sterilize the object of pathogens without causing ambient atmosphere in chamber 9 to reach the temperature sufficient to sterilize the object of pathogens wherein the heating elements 15A,15B comprise Nichrome wire housed in a sealed tube that consists essentially of quartz and generate infrared radiation at a wavelength of about 3.23 micron.

10. The method of claim 9 wherein the object is any of hamburger meat, ground meat, beef, poultry, and pork.

11. The method of claim 9 wherein the pathogen is any of *E. Coli* O157:H7, *E. Coli*(EXEC), and *salmonella*.

12. The method of claim 9 wherein the temperature is about 158° F. to about 176° F.

13. The method of claim 9 wherein the heating elements 15A,15B generate infrared radiation at an intensity of about 20 KW/m$^2$ to about 50 KW/m$^2$.

14. The method of claim 13 wherein the heating elements 15A,15B cause the products to be sterilized to reach about 160° C.

15. The method of claim 9 wherein the pathogen is any of *Salmonella, E. Coli* 0157:H7, *E. Coli* (EXEC), hepatitis, anthrax, and prions.

* * * * *